US00PP30384P3

(12) United States Plant Patent
Ya'Akov et al.

(10) Patent No.: US PP30,384 P3
(45) Date of Patent: Apr. 16, 2019

(54) AVOCADO TREE NAMED 'TAMI'

(50) Latin Name: ***Persea americana* P. Mill.**
Varietal Denomination: TAMI

(71) Applicant: State of Israel, Ministry of Agriculture & Rural Development, Agricultural Research Organization, Rishon Lezion (IL)

(72) Inventors: Avraham Ben Ya'Akov, Pardes Hana (IL); Miriam Silberstein, Pardes-Hana (IL); Vered Irihimovitch, Modiin (IL)

(73) Assignee: State of Israel, Ministry of Agriculture & Rural Development, Agricultural Research Organization, Rishon Lezion (IL)

( * ) Notice: Subject to any disclaimer, the term of this patent is extended or adjusted under 35 U.S.C. 154(b) by 0 days.

(21) Appl. No.: 15/330,547

(22) Filed: Oct. 7, 2016

(65) Prior Publication Data

US 2018/0103567 P1 Apr. 12, 2018

(51) Int. Cl.
*A01H 5/08* (2018.01)

(52) U.S. Cl.
USPC ..... Plt./200
CPC ..... *A01H 5/08* (2013.01)

(58) Field of Classification Search
USPC ..... Plt./200
See application file for complete search history.

(56) References Cited

PUBLICATIONS

Ben-Ya'acov and Zilberstaine. 1999. Revista Chapingo Serie Horticultura 5: 39-42.*

* cited by examiner

*Primary Examiner* — Keith O. Robinson
(74) *Attorney, Agent, or Firm* — Foley & Lardner LLP

(57) ABSTRACT

A new and distinct avocado of *Persea americana* P. Mill. named 'TAMI', particularly characterized by *Phytophthora cinnamomi* resistance.

4 Drawing Sheets

Figure 1:
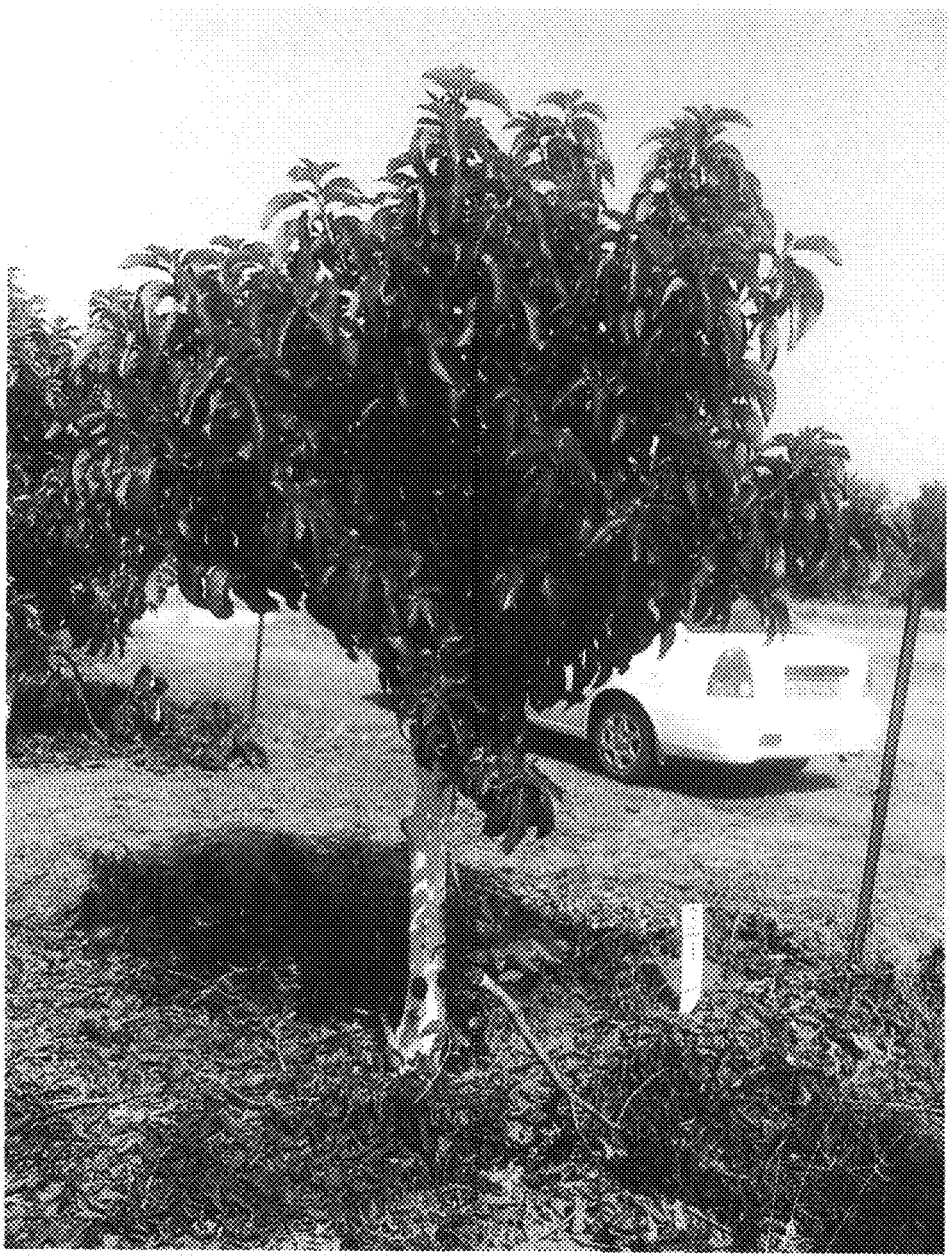

Botanical name of the genus and species of the plant claimed: *Persea americana* P. Mill.

Variety denomination: 'TAMI'.

BACKGROUND OF THE INVENTION

The present invention relates to a new and distinct variety of avocado tree, botanically known as *Persea americana* P. Mill. of the Lauraceae family, and hereinafter referred to by the variety denomination 'TAMI'.

Clonal avocado rootstocks were developed in Israel on a small scale between the years 1962 to 1977 and on a large scale in the years following. During the entire period about 220 different rootstocks have been developed in an attempt to solve soil problems caused by stress factors such as salinity, lime, poor aeration and root-rot, and various combinations of these factors, while simultaneously improving productivity. Uniformity among trees and dwarfness were also taken into account as part of the search for better rootstocks. The development process included field evaluation on a very large scale, in which 350 experiments and 65000 trees took part.

The new *Persea americana* P. Mill. 'TAMI' was selected by the inventors, Avraham Ben Ya'akov, Miriam Silberstein, and Vered Irihimovitch, growing in a cultivated area in the late 1970's in Givat Haim, Israel. The new *Persea americana* P. Mill. 'TAMI' was selected by the inventors based on *Phytophthora cinnamomi* resistance.

Asexual propagation of the new *Persea americana* P. Mill. variety by the Frolich method for vegetative propagation was first performed in March 1985 in the Volcani Center, Israel, and has demonstrated that the combination of characteristics as herein disclosed for the new variety are firmly fixed and retained through successive generations of asexual propagation. The new variety propagates true-to-type.

BRIEF DESCRIPTION OF THE INVENTION

The following traits have been repeatedly observed and are determined to be characteristics of 'TAMI' which in combination distinguish this avocado tree as a new, unique and distinct variety:

1. *Phytophthora cinnamomi* resistance;

Of the many varieties known to the present inventors, the most similar in comparison to the new *Persea americana* P. Mill. 'TAMI' is *Persea americana* P. Mill. 'Degania 117' (unpatented) which differ from the new avocado 'TAMI' in the characteristics described in Table 1:

TABLE 1

Comparison with most similar variety.

| Characteristic | New Variety 'TAMI' | Comparison Variety 'Degania 117' |
|---|---|---|
| *Phytophthora cinnamomi* tolerance | High | High sensitivity |
| Lime chlorosis resistance | Medium | High |

TABLE 1-continued

| Comparison with most similar variety. | | |
|---|---|---|
| Characteristic | New Variety 'TAMI' | Comparison Variety 'Degania 117' |
| Tree vigor characteristic | medium | Vigorous type |

BRIEF DESCRIPTION OF THE PHOTOGRAPHS

The accompanying photographs illustrate the overall appearance of the new *Persea americana* P. Mill. variety 'TAMI' showing the colors as true as is reasonably possible with colored reproductions of this type. Colors in the photographs may differ slightly from the color values cited in the detailed morphological description, which accurately describe the color of 'TAMI'. Plants shown in the photographs are approximately two years old.

FIG. 1—Shows a typical tree of 'TAMI'.

Figure 2:
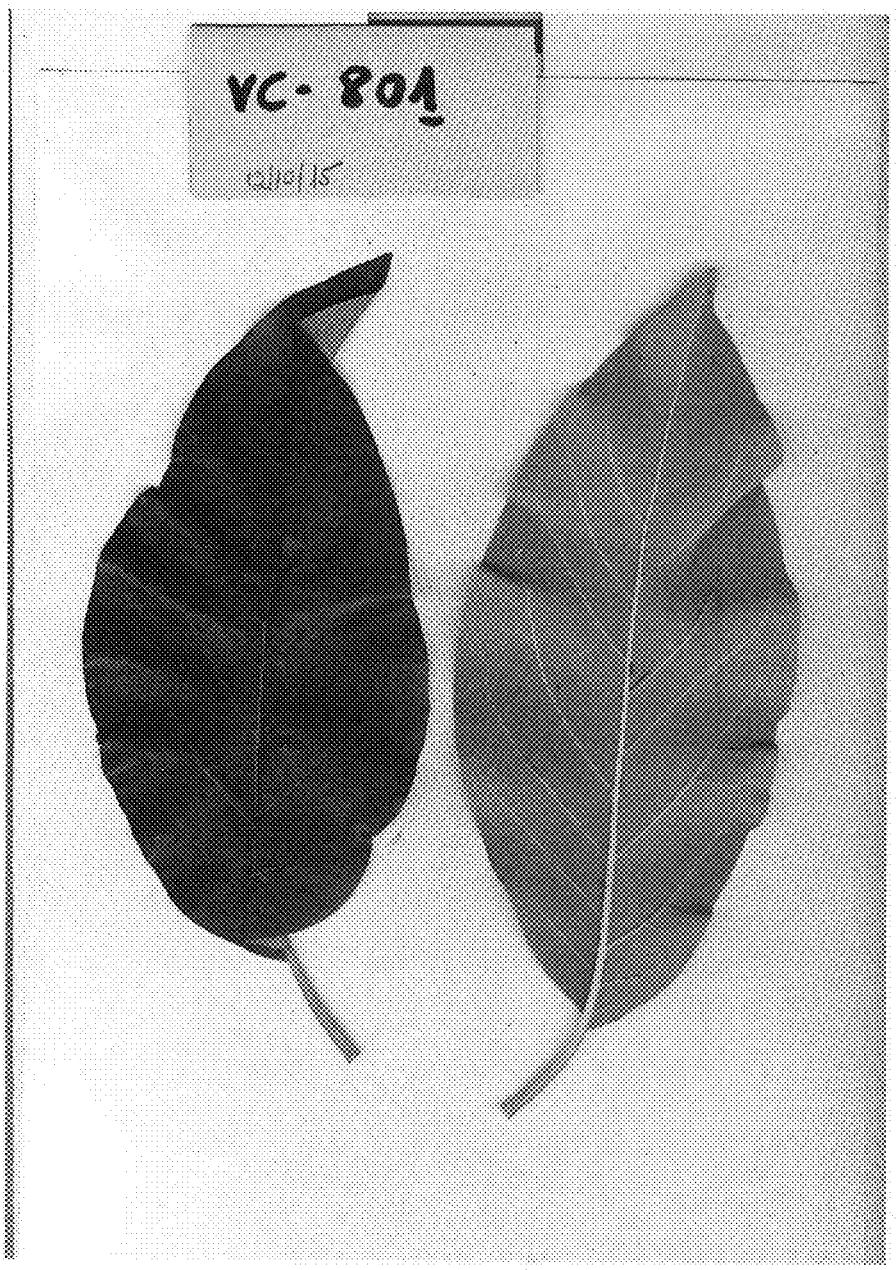

FIG. 2—Shows a typical leaf upper surface (left) and under surface (right) of 'TAMI'.

Figure 3:
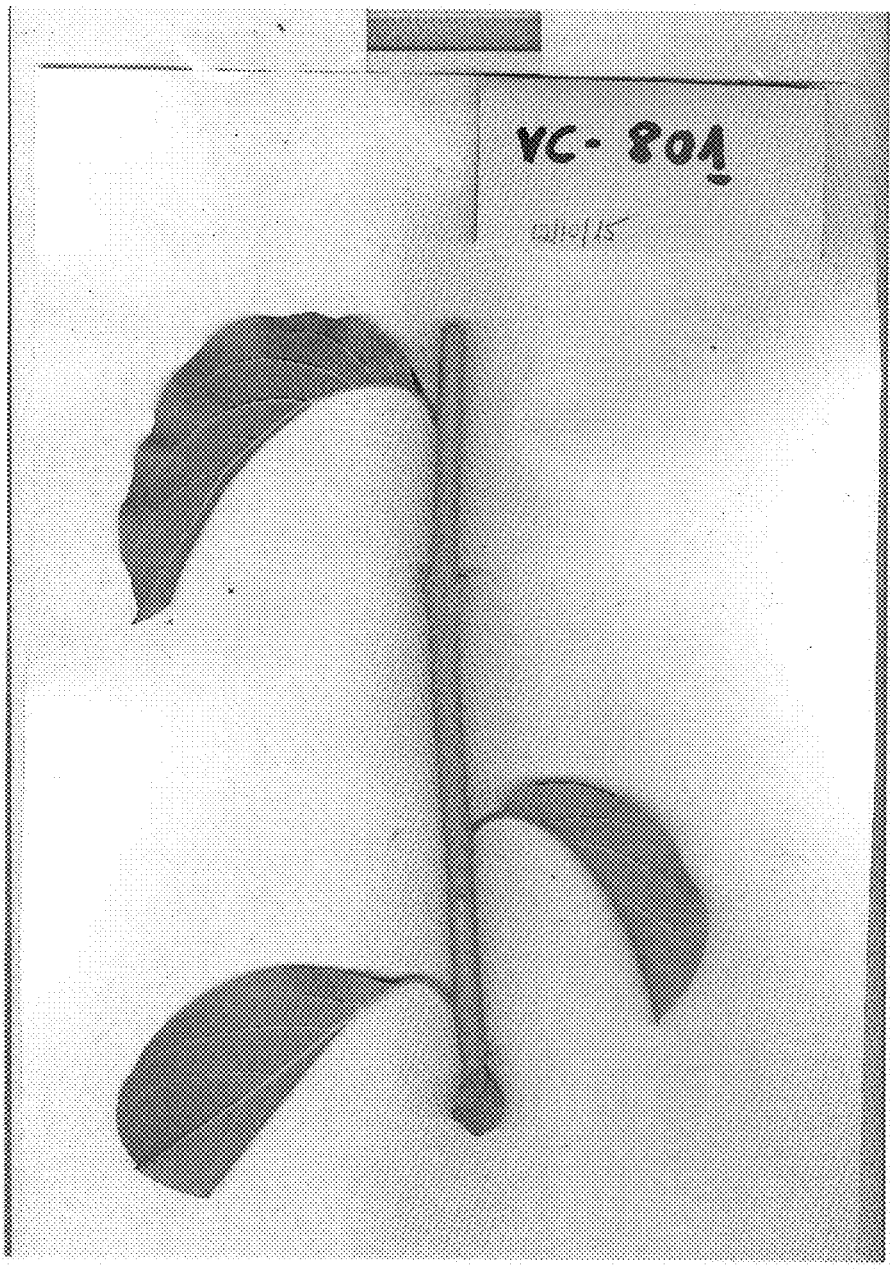

FIG. 3—Shows a typical shoot with leaves of 'TAMI'.

Figure 4:
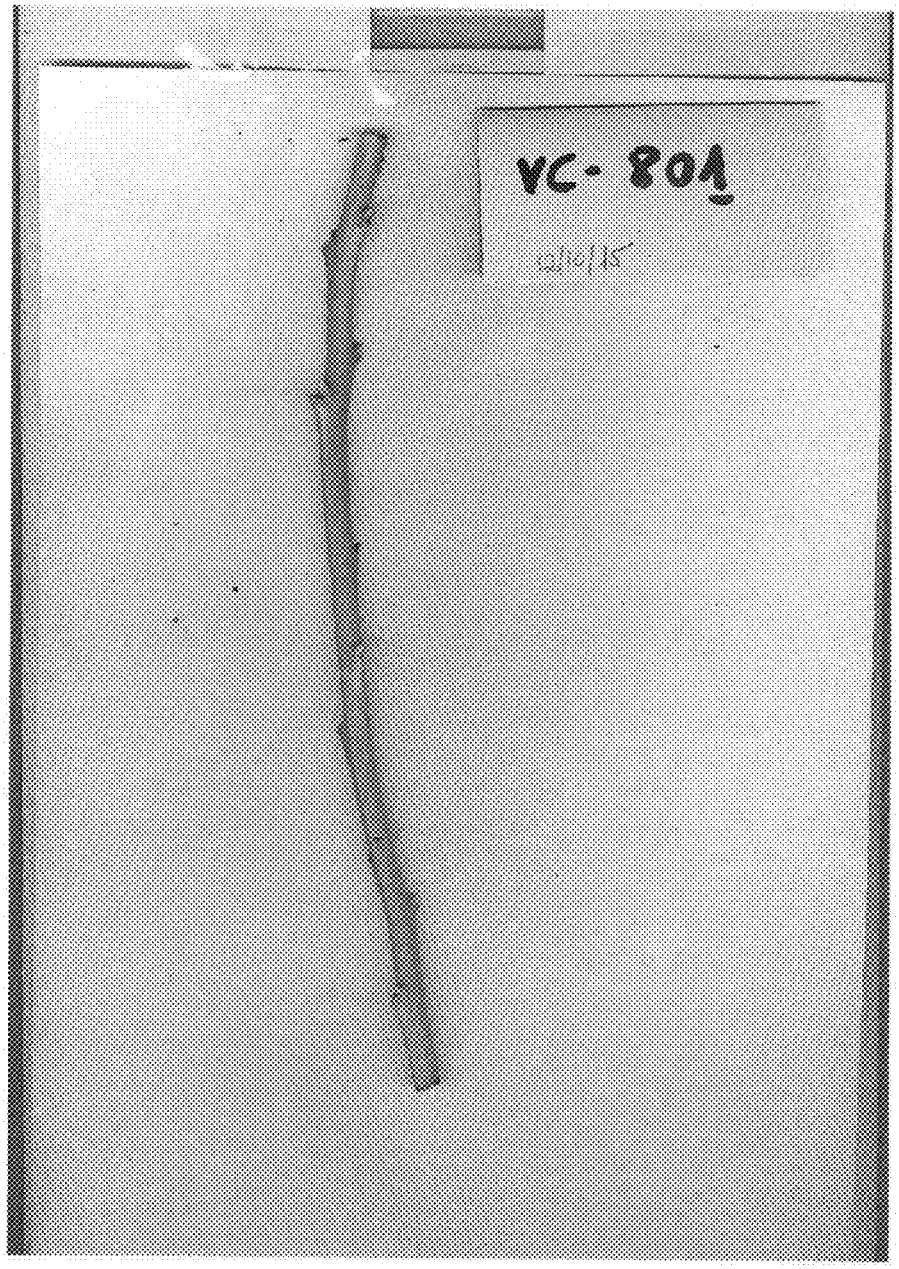

FIG. 4—Shows a typical vegetative bud of 'TAMI'.

DETAILED BOTANICAL DESCRIPTION

The new *Persea americana* P. Mill. 'TAMI' has not been observed under all possible environmental conditions. The phenotype of the new variety may vary with variations in environment such as temperature, light intensity, day length, soil or pruning without any change in the genotype of the avocado plant.

The aforementioned photographs, together with the following observations, measurements and values describe trees of 'TAMI' as grown in the orchard in the Volcani Center, Israel, under conditions which closely approximate those generally used in commercial practice. The described plants were propagated by the Frolich method and planted at a distance of 6×4 m in sandy red loam soil at an elevation of about 30 meters above sea level with 700-1000 m3 per dunam per season of irrigation and N:P:K 30:30:5 of fertilizers. Average annual rainfall is about 550 mm, with an average 350 mm of rainfall in winter (December to February). Mean diurnal minimum temperature in January is 7.2° C., and mean diurnal maximum temperature in July is 30.8° C.

Unless otherwise stated, the detailed morphological description includes observations, measurements and values taken from 2014 to 2015 and based on two-year-old 'TAMI' plants/trees grown in the orchard in the Volcani Center, Israel. Quantified measurements are expressed as an average or a range of measurements taken from a number of plants of 'TAMI'. The measurements of any individual plant, or any group of plants, of the new variety may vary from the stated average or range.

Color references are made to The Royal Horticultural Society Colour Chart (R.H.S.), (1986 edition), except where general colors of ordinary significance are used. Color values were taken under daylight conditions in full sunlight in the Volcani Center, Israel.

All of the plants of 'TAMI', insofar as they have been observed, have been consistent in all the characteristics described below.

Classification:

*Botanical.*—*Persea americana* P. Mill.

Propagation: Frolich method.

Growing conditions:

*Light intensities.*—Full sunlight.

| | Jan | February | March | April | May | June | July |
|---|---|---|---|---|---|---|---|
| Mean maximum air temperature (° C.) | 17.8 | 18.1 | 20.1 | 24.5 | 27 | 29.2 | 30.8 |
| Mean minimum air temperature (° C.) | 7.2 | 7.1 | 8.8 | 11.5 | 14.6 | 17.9 | 20.6 |
| Mean rainfall (mm) | 140.5 | 96.9 | 66.1 | 17.5 | 2.2 | — | — |

| | August | September | October | November | December |
|---|---|---|---|---|---|
| Mean maximum air temperature (° C.) | 31.2 | 30.4 | 28.3 | 24.1 | 19.7 |
| Mean minimum air temperature (° C.) | 21.2 | 19.4 | 16 | 11.8 | 8.6 |
| Mean rainfall (mm) | — | 0.4 | 20.4 | 76.2 | 130.3 |

*Fertilization.*—A balanced fertilizer with level of N:P:K 30:30:5.

Growth regulators: As used in commercial practice.

TABLE OF CHARACTERISTICS

TREE:
Age: Observed trees were two years old.

| | |
|---|---|
| Tree | Type: West Indian.<br>Vigor: strong.<br>Growth habit: semi-upright.<br>General shape: erect.<br>Density of canopy: dense.<br>Height: about 2 m.<br>Number of main branches: 2. |
| Main branch | Attitude: upright. |
| Trunk | Diameter at 50 cm height: about 20 cm.<br>Surface Texture: Very rough<br>Bark color: RHS 199B<br>Lenticels: Not visible |
| Young shoot | Color: medium green RHS 144 A.<br>Color of lenticel: medium green RHS 137 C.<br>Shape of lenticels: elongated.<br>Density of lenticels: medium.<br>Size of lenticel: about 1 mm. |
| Shoot | Length of internode: 55-70 cm.<br>Thickness: 12-15 mm.<br>Color: medium green RHS 144 A. |
| Vegetative bud | Shape: conical.<br>Length: 2-3 mm.<br>Color: medium yellow green RHS 153 A.<br>Pubescence: medium. |
| Young leaf | Color of pubescence of petiole: white, RHS 155B.<br>Color of upper side: medium to dark green RHS 137 A.<br>Color of lower side: medium green RHS 147 B. |
| Leaf | Attitude relative to shoot: horizontal to semi upright. |
| Leaf blade | Length: 17-22 cm.<br>Width: 67-87 mm.<br>Ratio length/width: longer than broad.<br>Shape: long ovate.<br>Shape of apex: acute.<br>Tip: acuminate.<br>Color of upper side: very dark green RHS 139 A. |

-continued

TABLE OF CHARACTERISTICS

TREE:
Age: Observed trees were two years old.

| | |
|---|---|
| | Color of lower side: medium green RHS 138 B. |
| | Anthocyanin coloration: absent. |
| | Shape in cross section: concave. |
| | Shape of base: rounded. |
| | Twisting along whole length: absent. |
| | Twisting of apex: present. |
| | Undulation of margin: strong. |
| | Relief of venation on upper surface: at level. |
| | Relief of venation on lower surface: raized. |
| | Color of veins of upper side: light green RHS 144 B. |
| | Color of veins of lower side: light green RHS 145 C. |
| | Number of secondary veins: 5 or 6 or 7. |
| | Distance of secondary veins: 2-3.5 cm. |
| | Density of pubescence on upper surface: sparse. |
| | Density of pubescence on lower surface: medium. |
| | Color of hairs: white, RHS 155B. |
| | Anise aroma: absent. |
| Petiole | Length: about 30 mm. |
| | Thickness: 2-3 mm. |
| | Color: light green RHS 144 B. |
| | Pubescence: weak. |
| | Cross section: rounded and truncate. |
| Inflorescence | Flowering Period: end March to mid April |
| | Diameter: 25-31 cm |
| | Length of Main Axis: 10-16 mm |
| | Thickness of Main Axis: 5-7 mm |
| | Number of Branches: 3 to 7 |
| | Length of Lowest Branch: 15-18 cm |
| | Pubescence: Medium |
| | Color: RHS 145C |
| | Anthocyanin Coloration: Absent |
| | Lenticel size: 1-2 mm |
| | Lenticel shape: Elongated |
| | Lenticel color: RHS 144 A |
| | Nectary Position: Along axis |
| | Nectary size: 2-3 mm |
| | Nectary color: RHS 152 A |
| Flower | Pedicel Length: 5-7 mm |
| | Number of Petals: 6 |
| | Diameter: 5-11 mm |

-continued

TABLE OF CHARACTERISTICS

TREE:
Age: Observed trees were two years old.

| | |
|---|---|
| | Shape: Star-shaped |
| | Fragrance: None |
| Petal | Length: 2-3 mm |
| | Width: About 2 mm |
| | Shape: Triangular |
| | Upper Surface Color: RHS 145B |
| | Lower Surface Color: RHS 145 B |
| | Texture (Upper and Lower Surfaces): Smooth |
| Sepal | Position: Fused at base |
| | Shape: Triangular |
| | Length: 5-6 mm |
| | Width: About 2 mm |
| | Outer Surface Color: RHS 145 B |
| | Inner Surface Color: RHS 145 C |
| | Outer Surface Pubescence: Strong |
| | Inner Surface Pubescence: Not visible |
| Style | Number 1 to 3 |
| | Shape: Straight |
| | Length: 1-2 mm |
| | Color: RHS 153 D |
| | Pubescence: Not visible |
| Stamen | Number: 8 or 9 |
| | Filament Length: 1-2 mm |
| | Filament color: RHS 145 C |
| | Filament texture: Smooth; no pubescence |
| | Anther Size: 1-2 mm |
| | Anther Shape: elongated |
| | Anther Color: RHS 13 B |
| | Pollen Color: RHS 13 A |

Disease resistance: *Phytophthora cinnamomi* resistance.
Pest resistance: No atypical resistance has been noted.
Disease susceptibility: None observed.
Pest susceptibility: None observed.

We claim:

1. A new and distinct avocado variety of *Persea americana* P. Mill. named 'TAMI', as illustrated and described herein.

* * * * *